US012811002B2

(12) United States Patent
Eckhouse et al.

(10) Patent No.: US 12,811,002 B2
(45) Date of Patent: Nov. 24, 2026

(54) ANALYZING ACTIONS, AUTOMATIC CORRECTION OF ACTIONS, AND DECISION SUPPORT AND AUTOMATION DURING ENDOVASCULAR PROCEDURES

(71) Applicant: RAPID MEDICAL LTD., Yokneam (IL)

(72) Inventors: Ronen Eckhouse, Yokneam (IL); Yuval Vaknin, Yokneam (IL); Matan Gedulter, Yokneam (IL); Giora Kornblau, Yokneam (IL)

(73) Assignee: RAPID MEDICAL LTD., Yokneam (IL)

( * ) Notice: Subject to any disclaimer, the term of this patent is extended or adjusted under 35 U.S.C. 154(b) by 22 days.

(21) Appl. No.: 18/719,161

(22) PCT Filed: Dec. 13, 2022

(86) PCT No.: PCT/IB2022/062139
§ 371 (c)(1),
(2) Date: Jun. 12, 2024

(87) PCT Pub. No.: WO2023/111844
PCT Pub. Date: Jun. 22, 2023

(65) Prior Publication Data

US 2024/0420833 A1 Dec. 19, 2024

Related U.S. Application Data

(60) Provisional application No. 63/265,331, filed on Dec. 13, 2021.

(51) Int. Cl.
*G16H 40/40* (2018.01)
*G16H 30/40* (2018.01)

(52) U.S. Cl.
CPC ............. *G16H 40/40* (2018.01); *G16H 30/40* (2018.01)

(58) Field of Classification Search
CPC ............................... G16H 40/40; G16H 30/40
(Continued)

(56) References Cited

U.S. PATENT DOCUMENTS 8,956,352 B2 * 2/2015 Mauch .............. A61M 25/0147 606/41
9,623,211 B2 * 4/2017 Hendrick ............... A61B 90/98
(Continued)

FOREIGN PATENT DOCUMENTS

JP 2020512034 A 4/2020
WO 2006039511 A2 4/2006
WO 2023037221 A1 3/2023

OTHER PUBLICATIONS

International Search Report and Written Opinion issued on May 12, 2023 in counterpart International Patent Application No. PCT/IB2022/062139 (19 pages, in English).
(Continued)

*Primary Examiner* — Michael Tomaszewski
(74) *Attorney, Agent, or Firm* — Sterne, Kessler, Goldstein & Fox P.L.L.C.

(57) ABSTRACT

A non-transitory computer readable medium containing instructions that when executed by at least one processor, cause the at least one processor to provide automation of an endovascular procedure, is provided. The operations include receiving a medical image captured prior to or during an invasive procedure; analyzing the medical image to detect one or more of a body structure and a portion of an endovascular device in the body structure; based on the detected one or more of the body structure and the portion of the endovascular device in the body structure, selecting an
(Continued)

action for controlling the endovascular device during the invasive procedure; and causing a performance of the selected action.

24 Claims, 6 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 10,661,053 | B2 | 5/2020 | Yang et al. | |
| 10,729,502 | B1 * | 8/2020 | Wolf | G16H 15/00 |
| 2002/0058868 | A1 * | 5/2002 | Hoshino | G01R 33/287 600/414 |
| 2003/0040737 | A1 | 2/2003 | Merril et al. | |
| 2003/0208188 | A1 | 11/2003 | Ritter et al. | |
| 2006/0258935 | A1 * | 11/2006 | Pile-Spellman | A61B 5/6885 600/416 |
| 2009/0005675 | A1 * | 1/2009 | Grunwald | A61B 34/20 600/467 |
| 2010/0069841 | A1 * | 3/2010 | Miesel | A61M 5/14276 604/111 |
| 2011/0257593 | A1 * | 10/2011 | Kalpin | A61M 5/14276 604/111 |
| 2012/0136242 | A1 | 5/2012 | Qi et al. | |
| 2012/0143293 | A1 * | 6/2012 | Mauch | A61M 25/0074 607/101 |
| 2012/0245595 | A1 | 9/2012 | Kesavadas et al. | |
| 2012/0296262 | A1 | 11/2012 | Ogata et al. | |
| 2014/0058191 | A1 | 2/2014 | Zilbershlag | |
| 2014/0275982 | A1 * | 9/2014 | Hendrick | A61B 5/064 606/130 |
| 2015/0080875 | A1 * | 3/2015 | Kasprzyk | A61B 18/1815 606/33 |
| 2017/0027604 | A1 * | 2/2017 | Wallace | A61B 17/22 |
| 2017/0049959 | A1 * | 2/2017 | Eitan | A61M 5/142 |
| 2018/0214669 | A1 * | 8/2018 | Davies | A61M 25/0147 |
| 2019/0365252 | A1 * | 12/2019 | Fernald | A61B 5/004 |
| 2019/0388108 | A1 * | 12/2019 | Ferrera | A61B 17/221 |
| 2020/0093973 | A1 * | 3/2020 | Gandhi | A61M 60/13 |
| 2020/0268457 | A1 * | 8/2020 | Wolf | G16H 15/00 |
| 2020/0289136 | A1 * | 9/2020 | Chou | A61B 17/22 |
| 2020/0302600 | A1 * | 9/2020 | Barral | G06V 20/70 |
| 2021/0137634 | A1 * | 5/2021 | Lang | A61B 34/20 |
| 2021/0282950 | A1 * | 9/2021 | MacTaggart | A61B 5/027 |
| 2021/0361357 | A1 | 11/2021 | Crawford | |
| 2022/0105639 | A1 | 4/2022 | Zhang et al. | |
| 2022/0151625 | A1 | 5/2022 | Kaufman et al. | |
| 2023/0010350 | A1 | 1/2023 | Peine et al. | |
| 2023/0080060 | A1 * | 3/2023 | Ayvali | A61B 34/25 318/568.21 |
| 2023/0317248 | A1 * | 10/2023 | Braido | A61B 17/3209 705/2 |
| 2024/0164801 | A1 * | 5/2024 | Wainwright | A61B 17/22 |
| 2024/0197347 | A1 | 6/2024 | Saadat et al. | |
| 2024/0420833 | A1 * | 12/2024 | Eckhouse | G16H 30/40 |
| 2025/0049510 | A1 * | 2/2025 | Eckhouse | A61B 17/22 |
| 2026/0000497 | A1 * | 1/2026 | Sudin | A61F 2/0108 |

OTHER PUBLICATIONS

Extended European Search Report for European Application No. EP22906786.3, mailed on Feb. 6, 2026, 13 pages.
International Search Report issued on Mar. 8, 2023 in counterpart International Patent Application No. PCT/IB2022/062141.

* cited by examiner

600

ANALYZING ACTIONS, AUTOMATIC CORRECTION OF ACTIONS, AND DECISION SUPPORT AND AUTOMATION DURING ENDOVASCULAR PROCEDURES

CROSS-REFERENCE TO RELATED APPLICATIONS

This application claims the benefit of priority to U.S. Provisional Application 63/265,331, filed Dec. 13, 2021, which is incorporated herein by reference in its entirety.

TECHNICAL FIELD

The present disclosure, in some embodiments thereof, relates to analyzing the actions of users during endovascular procedures, automatic correction to the actions of users during endovascular procedures, and decision support and automation during endovascular procedures.

BACKGROUND

Interventional radiology has gained popularity in many medical fields, such as endovascular intervention techniques including in the endovascular treatment of acute conditions (e.g., ischemic stroke, trauma, gastrointestinal tract bleeding, and aortic aneurysm) and elective embolization (e.g., coil embolization repair of aneurysm and embolization of uterine and prostate arteries). Many different medical devices have been developed for these treatment modalities, and their effective use is essential to the success of treatment. Accordingly, training and supporting interventional radiologists as well as maintaining their high skill is vitally important to the success of treatment.

SUMMARY

Gathering and analyzing information related to actions of users for controlling medical devices, including endovascular devices, during invasive procedures may improve the quality and success rate of invasive procedures. The analysis can be used, for example, to compare the actions of the interventional radiologist to their previous action, to other radiologists working in the same medical field, or to gold standard values. The comparison may be used to improve radiologist's actions by providing them with suggestions for decision making, also known as decision support. Furthermore, such an analysis may be used, for example, as part of a training protocol to provide a safe and unified practice for users such as interventional radiologists.

Additionally, the gathering and analyzing of information may be used to influence an automatic correction to actions of a user of an endovascular device during an invasive procedure. Further, the information gathered and analyzed may be used to automate an endovascular procedure. For example, information from medical images and/or sensors can be used to automate a procedure. The user may identify certain information or parameters associated with the procedure or the outcome and the endovascular device may be automated to perform actions corresponding to the information or parameters.

Embodiments of the present disclosure may include a non-transitory computer readable medium containing instructions that when executed by at least one processor, cause the at least one processor to analyze actions of a user of an endovascular device during an invasive procedure. The operations may include receiving indications of a plurality of actions of a user for controlling an endovascular device during an invasive procedure using a control device of the endovascular device; receiving an indication of a preceding status for each action of the plurality of actions; generating data related to the plurality of actions of the user, the data including a type of action and the preceding status for each action; analyzing the data to determine a relation between the preceding status for each action and the plurality of actions; and using the determined relation between the preceding status for each action and the plurality of actions to provide an evaluation of the user.

In some embodiments, a system for analyzing actions of a user of an endovascular device during an invasive procedure is provided. The system may include a processor configured to receive indications of a plurality of actions of a user for controlling an endovascular device during an invasive procedure using a control device of the endovascular device; receive an indication of a preceding status for each action of the plurality of actions; generate data related to the plurality of actions of the user, the data including a type of action and the preceding status for each action; analyze the data to determine a relation between the preceding status for each action and the plurality of actions; and use the determined relation between the preceding status for each action and the plurality of actions to provide an evaluation of the user.

In other embodiments, a method for analyzing actions of a user of an endovascular device during an invasive procedure is provided. The method may include receiving indications of a plurality of actions of a user for controlling an endovascular device during an invasive procedure using a control device of the endovascular device; receiving an indication of a preceding status for each action of the plurality of actions; generating data related to the plurality of actions of the user, the data including a type of action and the preceding status for each action; analyzing the data to determine a relation between the preceding status for each action and the plurality of actions; and using the determined relation between the preceding status for each action and the plurality of actions to provide an evaluation of the user.

Embodiments of the present disclosure may include a non-transitory computer readable medium containing instructions that when executed by at least one processor, cause the at least one processor to perform automatic correction of an action of a user of an endovascular device during an invasive procedure. The operations may include receiving an indication of a magnitude and a type of the action of the user for controlling an endovascular device during an invasive procedure using a control device of the endovascular device; determining a correction to the magnitude of the action based on the type of the action and one or more parameters associated with the type of the action; and overriding the action of the user based on the determined correction to the magnitude, wherein the override is configured to transform the endovascular device in response to the action.

In some embodiments, a system for automatic correction of an action of a user of an endovascular device during an invasive procedure is provided. The system may include a processor configured to receive an indication of a magnitude and a type of the action of the user for controlling an endovascular device during an invasive procedure using a control device of the endovascular device; determine a correction to the magnitude of the action based on the type of the action and one or more parameters associated with the type of the action; and override the action of the user based on the determined correction to the magnitude, wherein the override is configured to transform the endovascular device in response to the action.

In other embodiments, a method for automatic correction of an action of a user of an endovascular device during an invasive procedure is provided. The method may include receiving an indication of a magnitude and a type of the action of the user for controlling an endovascular device during an invasive procedure using a control device of the endovascular device; determining a correction to the magnitude of the action based on the type of the action and one or more parameters associated with the type of the action; and overriding the action of the user based on the determined correction to the magnitude, wherein the override is configured to transform the endovascular device in response to the action.

Embodiments of the present disclosure may include a non-transitory computer readable medium containing instructions that when executed by at least one processor, cause the at least one processor to perform operations relating to a recommended action during an endovascular procedure. The operations may include receiving a medical image captured prior to or during an invasive procedure; analyzing the medical image to detect one or more of a body structure and a portion of an endovascular device in the body structure; based on the detected one or more of the body structure and the portion of the endovascular device in the body structure, selecting the recommended action for controlling the endovascular device using a control device during the invasive procedure; and providing a set of instructions to perform the recommended action.

In some embodiments, a system for performing operations relating to a recommended action during an endovascular procedure is procedure. The system may include a processor configured to receive a medical image captured prior to or during an invasive procedure; analyze the medical image to detect one or more of a body structure and a portion of an endovascular device in the body structure; based on the detected one or more of the body structure and the portion of the endovascular device in the body structure, select the recommended action for controlling the endovascular device using a control device during the invasive procedure; and provide a set of instructions to perform the recommended action.

In other embodiments, a method for performing operations relating to a recommended action during an endovascular procedure is provided. The method may include receiving a medical image captured prior to or during an invasive procedure; analyzing the medical image to detect one or more of a body structure and a portion of an endovascular device in the body structure; based on the detected one or more of the body structure and the portion of the endovascular device in the body structure, selecting the recommended action for controlling the endovascular device using a control device during the invasive procedure; and providing a set of instructions to perform the recommended action.

Embodiments of the present disclosure may include a non-transitory computer readable medium containing instructions that when executed by at least one processor, cause the at least one processor to provide at least one recommendation to a user during endovascular procedures. The operations may include receiving a medical image captured prior to or during an invasive procedure; analyzing the medical image to detect one or more of the body structure and the portion of an endovascular in the body structure; based on the detected one or more of the body structure and the portion of the endovascular device in the body structure, selecting at least one recommendation for a prospective course of action; and during the invasive procedure, providing the at least one recommendation to a user performing the invasive procedure.

In some embodiments, a system for providing at least one recommendation to a user during endovascular procedures is provided. The system may include a processor configured to receive a medical image captured prior to or during an invasive procedure; analyze the medical image to detect one or more of the body structure and the portion of an endovascular in the body structure; based on the detected one or more of the body structure and the portion of the endovascular device in the body structure, select at least one recommendation for a prospective course of action; and during the invasive procedure, provide the at least one recommendation to a user performing the invasive procedure.

In other embodiments, a method for providing at least one recommendation to a user during endovascular procedures is provided. The method may include receiving a medical image captured prior to or during an invasive procedure; analyzing the medical image to detect one or more of the body structure and the portion of an endovascular in the body structure; based on the detected one or more of the body structure and the portion of the endovascular device in the body structure, selecting at least one recommendation for a prospective course of action; and during the invasive procedure, providing the at least one recommendation to a user performing the invasive procedure.

Embodiments of the present disclosure may include a non-transitory computer readable medium containing instructions that when executed by at least one processor, cause the at least one processor to provide automation of an endovascular procedure. The operations may include receiving a medical image captured prior to or during an invasive procedure; analyzing the medical image to detect one or more of a body structure and a portion of an endovascular device in the body structure; based on the detected one or more of the body structure and the portion of the endovascular device in the body structure, selecting an action for controlling the endovascular device during the invasive procedure; and causing a performance of the selected action.

In some embodiments, a system for automation of an endovascular procedure is provided. The system may include at least one processor configured to receive a medical image captured prior to or during an invasive procedure; analyze the medical image to detect one or more of a body structure and a portion of an endovascular device in the body structure; based on the detected one or more of the body structure and the portion of the endovascular device in the body structure, select an action for controlling the endovascular device during the invasive procedure; and cause a performance of the selected action.

In other embodiments, a method for automation of an endovascular procedure is provided. The method may include receiving a medical image captured prior to or during an invasive procedure; analyzing the medical image to detect one or more of a body structure and a portion of an endovascular device in the body structure; based on the detected one or more of the body structure and the portion of the endovascular device in the body structure, selecting an action for controlling the endovascular device during the invasive procedure; and causing a performance of the selected action.

Unless otherwise defined, technical and/or scientific terms used herein have the same or similar meaning as commonly understood by one of ordinary skill in the art to which the present disclosure pertains. Examples of methods and/or materials are described below, but methods and/or materials similar or equivalent to those described may be used in the practice and/or testing of embodiments of the present disclosure. In cases of conflict, the patent specification, including definitions, will control. The materials, methods, and examples are illustrative only and are not intended to be necessarily limiting.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

The accompanying drawings, which are incorporated in and constitute a part of this specification, illustrate disclosed embodiments and, together with the description, serve to explain the disclosed embodiments. The particulars shown are by way of example and for purposes of illustrative discussion of embodiments of the present disclosure. The description taken with the drawings makes apparent to those skilled in the art how embodiments of the present disclosure may be practiced.

DETAILED DESCRIPTION

Figure 1:
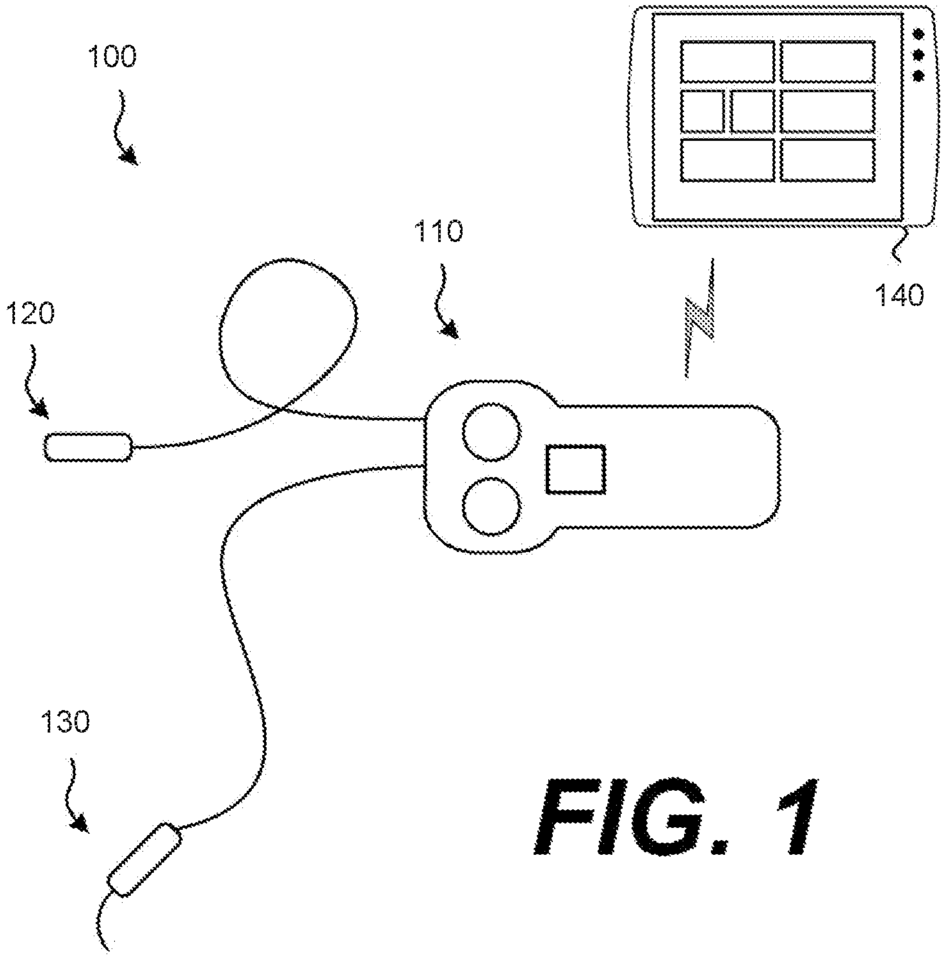
FIG. 1 illustrates an example of an endovascular device system with a control device, an endovascular device, a peripheral device, and a sensor, consistent with various embodiments of the present disclosure.

Examples of embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It should also be noted that as used in the present disclosure and in the appended claims, the singular forms "a," "an," and "the" include plural references unless the context clearly dictates otherwise.

Unless specifically stated otherwise, as apparent from the following description, throughout the specification discussions utilizing terms such as "processing," "calculating," "computing," "determining," "generating," "setting," "configuring," "selecting," "defining," "applying," "obtaining," "monitoring," "providing," "identifying," "segmenting," "classifying," "analyzing," "associating," "extracting," "storing," "receiving," "transmitting," or the like, include actions and/or processes of a computer that manipulate and/or transform data into other data, the data represented as physical quantities, for example such as electronic quantities, and/or the data representing physical objects. The terms "computer," "processor," "controller," "processing unit," "computing unit," and "processing module" should be expansively construed to cover any kind of electronic device, component or unit with data processing capabilities, including, by way of non-limiting example, a personal computer, a wearable computer, smart glasses, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as," "for instance" and variants thereof describe non-limiting embodiments of the presently disclosed subject matter. Reference in the specification to features of "embodiments," "one case," "some cases," "other cases" or variants thereof means that a particular feature, structure or characteristic described may be included in at least one embodiment of the presently disclosed subject matter. Thus, the appearance of such terms does not necessarily refer to the same embodiment(s). As used herein, the term "and/or" includes any and all combinations of one or more of the associated listed items. As used herein, the expressions "at least one of . . . or" or "one or more . . . and" may include each listed item individually or any combination of the listed items. For example, the expression "at least one of A, B, or C" may include any of A, B, or C alone or any combination of A, B, and C (e.g., A+B, A+C, B+C, or A+B+C).

Features of the presently disclosed subject matter, are, for brevity, described in the context of particular embodiments. However, it is to be understood that features described in connection with one embodiment are also applicable to other embodiments. Likewise, features described in the context of a specific combination may be considered separate embodiments, either alone or in a context other than the specific combination.

In embodiments of the presently disclosed subject matter, one or more stages illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

Examples of the presently disclosed subject matter are not limited in application to the details of construction and the arrangement of the components set forth in the following description or illustrated in the drawings. The subject matter may be practiced or carried out in various ways. Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings.

The drawings in this document may not be to any scale. Different figures may use different scales and different scales can be used even within the same drawing, for example different scales for different views of the same object or different scales for the two adjacent objects.

Consistent with disclosed embodiments, "at least one processor" may constitute any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random-Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

Disclosed embodiments may include and/or access a data structure. A data structure consistent with the present disclosure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

Embodiments of the present disclosure relate to systems for performing various operations or functions described herein, including analyzing actions, automatic correction of actions, and decision support and automation during endovascular procedures. Disclosed systems may be specially constructed for a particular purpose and/or may include at least one general-purpose processor selectively activated or configured by a software program executed by the at least one processor. In some embodiments, operations and functions performed by a disclosed system, or by at least one processor of a disclosed system, may additionally or alternatively be implemented as steps of a method or process or as operations performed when instructions contained in a non-transitory computer readable medium are executed (e.g., by at least one processor).

Embodiments of the present disclosure relate to methods for performing various operations or functions described herein, including analyzing actions, automatic correction of actions, and decision support and automation during endovascular procedures. Aspects of methods disclosed herein may be implemented electronically, such as by at least one processor, and may occur over a network that is wired, wireless, or both wired and wireless. Aspects of methods disclosed herein may additionally, or alternatively, be implemented using non-electronic means. In a broadest sense, disclosed methods are not limited to particular physical and/or electronic instrumentalities (except where specified in the present disclosure or in the claims presented herein), but rather may be accomplished using many differing instrumentalities. In some embodiments, the steps of methods disclosed herein may be performed by features of disclosed systems (e.g., by at least one processor of a system disclosed herein) or may be implemented as operations performed when instructions contained in a non-transitory computer readable medium are executed (e.g., by at least one processor).

Embodiments of the present disclosure relate to non-transitory computer readable media containing instructions for performing various operations or functions described herein, including analyzing actions, automatic correction of actions, and decision support and automation during endovascular procedures. Consistent with disclosed embodiments, non-transitory computer readable media may store program instructions executable by at least one processor and which, when executed, may cause the at least one processor to perform the steps and/or methods described herein. As used herein, a non-transitory computer readable medium may refer to any type of physical memory on which information or data readable by at least one processor can be stored. Examples may include random access memory (RAM), read-only memory (ROM), volatile memory, non-volatile memory, hard drives, CD ROMs, DVDs, flash drives, disks, and any other known physical storage medium. Singular terms, such as "memory" and "computer readable medium," may, in some embodiments, refer to multiple structures, such as a plurality of memories or computer readable media. A computer readable medium may store instructions for execution by at least one processor, including instructions for causing the processor to perform steps or stages consistent with an embodiment disclosed herein. Additionally, one or more computer readable media may be utilized in implementing a computer-implemented method. The term "computer readable medium" should be understood to include tangible items and exclude carrier waves and transient signals.

Embodiments of the present disclosure relate to endovascular devices and to systems, methods, and non-transitory computer readable media for analyzing actions, automatic correction of actions, and decision support and automation during endovascular procedures. As used herein, an endovascular device may refer to any device or instrument configured to be placed within or to operate inside a blood vessel or another body structure within a human body for a medical purpose, for example to diagnose and/or treat a patient. In disclosed embodiments, the body structure may include a hollow anatomical feature within the body of the patient. Non-limiting examples of a body structure include a blood vessel, capillary, aneurysm, esophagus, stomach, intestines, gallbladder, urethra, fallopian tubes, vaginal canal, urinary bladder, or any other hollow body structure. In some embodiments, an endovascular device may include any device or instrument configured to be used during, or to otherwise facilitate, endovascular surgeries and procedures, as described in greater detail herein. An endovascular device may be configured to deliver a device, drug, or material from a first location (e.g., a location outside the body) to a treatment site in a blood vessel or other body structure and/or to remove a device, object, or material (e.g., a blood clot or other obstruction) from a blood vessel or other body structure. Additionally, or alternatively, in some embodiments, an endovascular device may be configured to cause a temporary or permanent change or transformation at a treatment site in a blood vessel (e.g., dilating a narrowed blood vessel or ablating vascular tissue). Some non-limiting examples of endovascular devices consistent with the present disclosure may include catheters (e.g., aspiration catheters or guide catheters), microcatheters, balloon catheters, devices with an expandable mesh (e.g., devices with an adjustable mesh and/or stent retrievers), medical sheaths, guide wires (e.g., controllable guide wires), coils, endovascular revascularization devices, embolization devices, ablation devices, stents, stent retrievers or any other device configured to be placed within a blood vessel or other body structure.

Embodiments of the present disclosure relate generally to medical devices, methods and systems for treating occlusions in a body. More particularly, embodiments of the present disclosure relate to devices and methods for removing clots, including, but not limited to, emboli and thrombi from hollow body structures or organs, such as blood vessels. Additionally, or alternatively, embodiments of the present disclosure may also be utilized to dilate occluded hollow body structures or organs (e.g., blood vessels), as well as in other medical procedures where support of hollow body structures or organs (e.g., blood vessels) is desired. Examples of medical procedures include, but are not limited to, thrombectomy, vessel remodeling, vessel support, vessel dilation, angioplasty, and embolization of aneurysms. Furthermore, embodiments of the present disclosure may also be utilized to address other ailments to the vasculature of a body.

FIG. 1 illustrates an example of endovascular device system 100 with a control device 110, an endovascular device 120, a peripheral device 140, and a sensor 130, consistent with various embodiments of the present disclosure.

The endovascular device system 100 may be used by a user of an endovascular device during an invasive procedure. The user may be any medical staff member, such as but not limited to, an interventional radiologist, an interventional cardiologist, an interventional neurologist, a surgeon, a nurse and a technician.

Control device 110 may be connected to endovascular device 120. Endovascular device 120 may be a deflectable catheter (e.g., a guide catheter), a bendable guide wire (e.g., a controllable guide wire), an endovascular coil, an endovascular stent, a stent retriever (e.g., a controllable stent retriever), an adjustable mesh device, an endovascular neuromodulation device, an aspiration catheter, or any other intraluminal device. According to some embodiments, control device 110 may be configured to control more than one endovascular device 120 (e.g., concomitantly, or subsequent to one another). Control device 110 may be connected to endovascular device 120 with at least one wire, as shown in FIG. 1. In other embodiments, control device 110 may be wirelessly connected to endovascular device 120 via wireless connections and/or communication systems such as Bluetooth®, Wi-Fi, or other mobile communication systems. It is contemplated that other communication systems may be used for wireless communication between control device 110 and endovascular device 120.

Control device 110 may be configured to control endovascular device 120. In some embodiments, control device 110 may be positioned outside of the body of a patient and endovascular device 120 may be positioned within the body of the patient, such as within a body structure (e.g., a blood vessel).

Control device 110 may be connected to sensor 130. Sensor 130 may be a force sensor, a pressure sensor, an electrical resistance sensor, a temperature sensor, a position sensor, a motor sensor, a flow sensor, and/or other electronic device configured to detect a physical state of the body of a patient or a state of endovascular device 120. Furthermore, sensor 130 may provide a sensor reading that may be indicative of at least one of a force, a tension, a pressure, an electrical resistance, an electrical capacitance, an electrical inductance, an electric current, an electrical impedance, or a temperature. In some embodiments, control device 110 may be connected to sensor 130 with at least one wire, as shown in FIG. 1. In other embodiments, control device 110 may be wirelessly connected to sensor 130 (not shown) via wireless connections and/or communication systems such as Bluetooth®, Wi-Fi, or other mobile communication systems. It is contemplated that other communication systems may be used for wireless communication between control device 110 and sensor 130. According to another embodiment, control device 110 may not be connected to sensor 130, and thus be connected only to endovascular device 120. In some embodiments, control device 110 may be configured to receive input from endovascular device 120 and/or from sensor 130. The received input includes an input from a user performing a procedure with the endovascular device. In some embodiments, the input from the user may be obtained from at least one of a manual input mechanism (e.g., a button, keyboard, computer mouse, lever, joystick, foot switch or pedal, or touch screen), an audio input mechanism (e.g., a microphone device configured to recognize verbal commands), a graphical user interface (GUI), or any other interface for receiving input from a user specifying the first desired action of the endovascular device.

Peripheral device 140 may be a user interface. Peripheral device 140 may include at least one processor and a user interface, such as a visual display or graphical user interface (GUI). For example, peripheral device 140 may include a desktop computer, laptop computer, tablet, smartphone, surgical control device or panel, display screen, television, hand-held device, touchscreen device, or another appliance. In some embodiments, peripheral device 140 may provide information visually and/or audibly. According to some embodiments, peripheral device 140 may comprise an input structure such as, but not limited to, a button, a keyboard, a computer mouse, a lever, a joystick, or a touch screen.

According to some embodiments, peripheral device 140 may be connected to control device 110 wirelessly, as shown in FIG. 1, with at least one wire, or by a magnetic connection. The wireless connection may be via communication systems such as Bluetooth®, Wi-Fi, or other mobile communication systems. It is contemplated that other communication systems may be used for wireless communication between control device 110 and peripheral device 140. A magnetic connection may include at least one magnet disposed in control device 110 and at least a second magnet disposed in peripheral device 140, where generation of magnetic force between the at least one magnet and the at least second magnet forms the connection or association.

According to some embodiments, peripheral device 140 may be connected to sensor 130. Peripheral device 140 may be connected to sensor 130 wirelessly or with at least one wire. The wireless connection may be via communication systems such as Bluetooth®, Wi-Fi, or other mobile communication systems. It is contemplated that other communication systems may be used for wireless communication between control device 110 and sensor 130.

Figure 2:
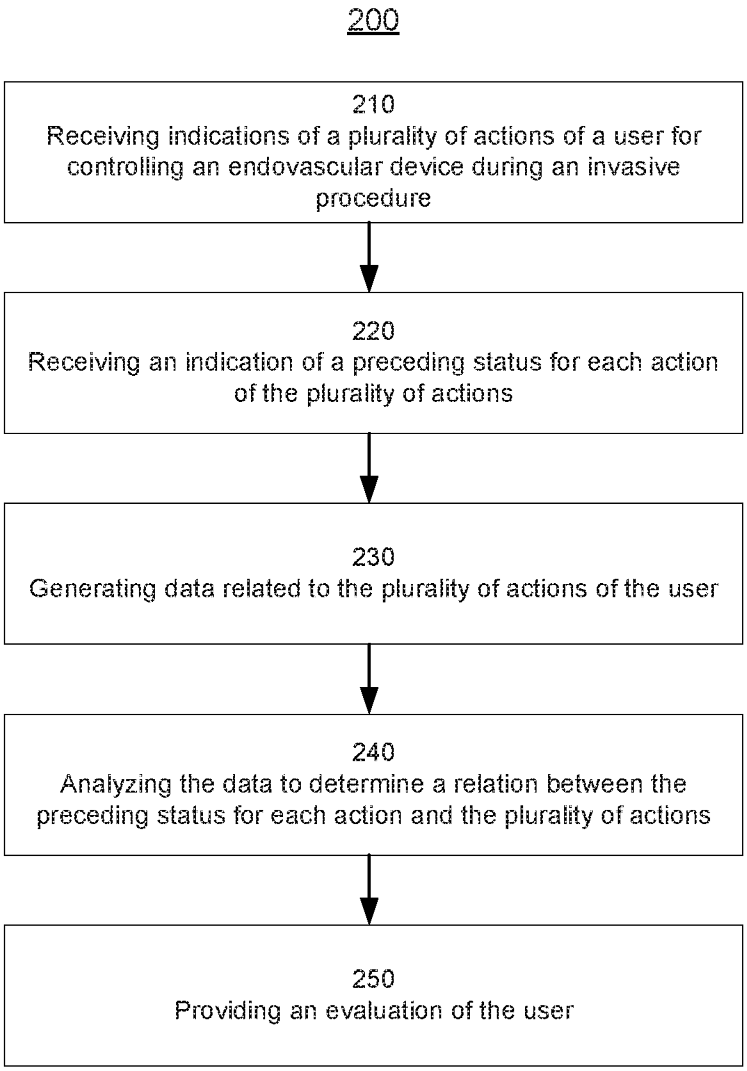
FIG. 2 presents a flowchart illustrating an example of a method for analyzing the actions of a user of an endovascular device during an invasive procedure, consistent with various embodiments of the present disclosure.

FIG. 2 presents a flowchart illustrating an example of a method for analyzing the actions of a user of an endovascular device during an invasive procedure 200, consistent with various embodiments of the present disclosure. The method shown in FIG. 2 and discussed below may be implemented as operations executed by a processor. The processor may be configured to execute instructions contained in a non-transitory computer readable medium. Alternatively, the processor may be part of a system. In some embodiments, the processor or more than one processor may evaluate information using artificial intelligence and inference rules, comparisons to information in a database, probabilities, and other methods of data analysis.

As shown in step 210, the method may include receiving indications of a plurality of actions of a user for controlling an endovascular device during an invasive procedure. The indications of the plurality of actions may be received from the control device, may be read from memory, may be received from an external device, or received from any other memory device or processor. The plurality of actions may include a movement or transformation of an endovascular device.

For example, the endovascular device may be a deflectable catheter or a bendable guide wire (e.g., controllable catheter or controllable guide wire). One of the plurality of actions may be an action configured to cause at least one distal portion (e.g., distal tip) of an endovascular device to bend. The bending of the distal portion (e.g., distal tip) of the endovascular device may permit the endovascular device to be navigated through tortuous anatomy, such as blood vessels, or other hollow body structures.

In another example, the endovascular device may be an endovascular stent retriever (e.g., controllable stent retriever) or an adjustable mesh device. One of the plurality of actions may be an action configured to cause a distal portion of the endovascular device (e.g., a mesh segment of the stent retriever or of the adjustable mesh device) to expand or contract. As used herein, expansion of a distal portion of the endovascular device may refer to an increase in the size or in at least one dimension of the endovascular device (e.g., an increase in an outer diameter, inner diameter, height, length or width of the distal portion of the endovascular device). Further, contraction may refer to a decrease in the size or in at least one dimension of the distal portion of the endovascular device, also referred to as collapse or relax. In some embodiments, the distal portion of the endovascular device may include a structure configured to expand and contract while the remainder of the device remains unchanged, such as an expandable mesh or stent or an inflatable balloon.

Another one of the plurality of the actions may be an action configured to control a magnitude of the expansion and/or a magnitude of the contraction of a distal portion of the endovascular device (e.g., a mesh segment of the stent retriever or of the adjustable mesh device). The expansion of the distal portion of the endovascular device may assist in capturing a clot, such as a blood clot in a body structure (e.g., in a blood vessel). Expansion of the distal portion of the endovascular device may also assist in support or remodeling of a body structure (e.g., blood vessel) during embolization of an aneurysm. Additionally, or alternatively, expansion of the distal portion of the endovascular device may enable mechanical dilation of vasospastic body structures (e.g., blood vessels). The expansion of the distal portion of the endovascular device (e.g., of a mesh segment) may also be used to treat arterial stenosis. The contraction of the distal portion of the endovascular device (e.g., of a mesh segment) may assist in safely removing the endovascular device from the body structure (e.g., blood vessel), and subsequently the body of the patient.

In another embodiment, the endovascular device may be a stent. One of the plurality of actions may be an action configured to cause a detachment of a stent in a body structure (e.g., blood vessel) of a patient.

According to some embodiments, the endovascular device may be an intraluminal device. In some embodiments, the endovascular device may be an endovascular coil. One of the plurality of actions may be an action configured to cause a detachment of the coil in a body structure of a patient (e.g., in a body lumen). In procedures such as coil embolization, the coil may be detached after packing an aneurysm to provide blood flow through a blood vessel (e.g., an artery or vein) and prevent blood flow through the aneurysm.

In some embodiments, the endovascular device may be an endovascular catheter or an endovascular coil. One of the plurality of actions may be an action configured to cause a portion of the endovascular device to heat up. For example, an endovascular catheter may be heated in the body of a patient to provide rapid and controlled rewarming in cases of hypothermia. As another example, an endovascular coil may be heated to cause a detachment of an endovascular coil during coil embolization.

In another embodiment, the endovascular device may be an endovascular neuromodulation device. One of the plurality of actions may be an action configured to cause an electric current to flow between two electrodes positioned within the body structure (e.g., blood vessel). Another one of the plurality of actions may be an action configured to cause a difference of electric potential between two electrodes positioned within a body structure (e.g., blood vessel). The actions associated with an endovascular neuromodulation device as discussed above may be configured to be performed at the same time, or simultaneously.

In some embodiments, one of the plurality of actions may be an action configured to cause a movement of the endovascular device, such as advancing forward into or backward out of the body structure (e.g., a blood vessel or other hollow body structure), or advancing one endovascular device over another endovascular device (e.g., movement of a catheter, such as an aspiration catheter or microcatheter, over a guide wire or a stent retriever).

As shown in step 220, the method may include receiving an indication of a preceding status for each action of the plurality of actions. The preceding status may occur immediately before the action, where immediate may include, for example, occurring within 1, 2, 3, 4 or 5 minutes before the action. For example, the preceding status may occur less than 1 second before the action, less than 5 seconds before the action, less than 10 seconds before the action, less than 15 seconds before the action, less than 20 seconds before the action, less than 30 seconds before the action, less than 45 seconds before the action, less than 60 seconds before the action, less than 90 seconds before the action, less than 120 seconds before the action, less than 150 seconds before the action, or less than 180 seconds before the action. In some embodiments, the preceding status may occur within 1 second to 2 minutes before the action.

In some embodiments, the preceding status may include a physical state of a patient. The physical state of a patient may include, for example, blood flow in a particular body structure (e.g., a blood vessel), a diameter of a particular portion of a particular body structure (e.g., a blood vessel), a blood perfusion to a particular tissue, a size of a body structure (e.g., a blood vessel) at a site of treatment, a location of a site of treatment, other anatomical or physiological descriptors of the patient, or any combination thereof. The physical state of a patient may further include information related to a clot in a body structure (e.g., in a blood vessel). The information related to the clot may include, for example, the type of the clot, the location of the clot within the body structure (e.g., a blood vessel), the size of the clot, or any combination thereof.

In other embodiments, the preceding status may include the state of the endovascular device. The state of the endovascular device may include, for example, a bending curvature at a distal portion of the endovascular device (e.g., at a distal tip), a degree of expansion or contraction of a distal portion of the endovascular device (e.g., a mesh segment), a temperature of the device, a flow of electrical current to flow two electrodes or points, a detachment of the device or part of the device in the body structure, and other physical and/or chemical descriptors of the endovascular device. The state of the endovascular device may further include a degree of opening associated with the endovascular device (e.g., of a mesh segment of the endovascular device), and/or a position of the endovascular device within a body structure.

In some embodiments, the preceding status may include an indication of an anatomical location of a portion of the endovascular device. The preceding status may include a location of a portion of endovascular device in relation to a clot, to an aneurysm, or to a narrowing of a body structure (e.g., blood vessel). In some embodiments, the preceding status may include a location of a portion of endovascular device in relation to a portion of a second endovascular device. Additionally, the preceding status may include a location of a portion of endovascular device in relation to a branch in a body structure (e.g., blood vessel).

A medical image captured before a particular action of the plurality of actions may be received and analyzed to determine the preceding status of a particular action. A medical image may be an angiogram, a computed tomography (CT) image, a magnetic resonance image (MRI), an X-ray, or an ultrasound image. A convolution of at least part of the medical image may be calculated. The value of the calculated convolution may be used to determine the preceding status of the particular action. In some embodiments, the medical image may be displayed on a display, for example, the peripheral device 140 of FIG. 1. In some embodiments, the medical image may be displayed on a separate display.

A sensor reading from a sensor may be captured before a particular action of the plurality of actions and analyzed to determine the preceding status of the particular action. In some embodiments, the sensor 130 may be connected to the endovascular device system 100, as shown in FIG. 1. In other embodiments, the sensor may be connected to the endovascular device 120. In some embodiments, the sensor may be connected to a display, for example, the peripheral device 140 of FIG. 1.

As shown in step 230, the method may include generating data related to the plurality of actions of the user. In some embodiments, the generated data may include a type of action and the preceding status for each action. The data may be generated based on the received indications of step 210. In another embodiment, the generated data may further include an outcome for each of the plurality of actions. An outcome for an action may be a predicted next action based on the current action.

The outcome may be an immediate outcome after the action, where immediate may include occurring, for example, within 1, 2, 3, 4 or 5 minutes after the action. For example, the outcome may occur less than 1 second after the action, less than 5 seconds after the action, less than 10 seconds after the action, less than 15 seconds after the action, less than 20 seconds after the action, less than 30 seconds after the action, less than 45 seconds after the action, less than 60 seconds after the action, less than 90 seconds after the action, less than 120 seconds after the action, less than 150 seconds after the action, or less than 180 seconds after the action. In some embodiments, the outcome may occur within 1 second to 2 minutes after the action.

In some embodiments, the outcome may include a modification to a physical state of a patient, as discussed above. In other embodiments, the outcome may include a modification to a state of the endovascular device, as discussed above.

The outcome may have an effect on a prognosis. A prognosis may include the speed of revascularization, or restoration of blood flow in a body structure (e.g., a blood vessel). For example, an action or a plurality of actions that correspond with efficient and/or quick clot retrieval may enable fast revascularization. An action or a plurality of actions that correspond with less efficient and/or slower clot retrieval may lead to slow revascularization. A fast revascularization may allow a patient to heal and/or recover with less long-term damage.

Another example of a prognosis may include the blocking of an aneurysm. An action or a plurality of actions that correspond with support of a body structure (e.g., blood vessel) during embolization of an aneurysm without blocking blood flow may enable fast recovery and successful treatment of an aneurysm. An action or a plurality of actions that correspond with blocking of blood flow during embolization of an aneurysm or with improper vessel support during embolization may lead to long-term damage and/or the need for a second corrective invasive procedure.

In some embodiments, a medical image captured after a particular action of the plurality of actions may be received and analyzed to determine the outcome of a particular action. A convolution of at least part of the medical image may be calculated. A value of the calculated convolution may be used to determine the outcome of a particular action.

In other embodiments, a sensor reading from the sensor may be captured after a particular action of the plurality of actions and analyzed to determine the outcome of the particular action.

In some embodiments, the generated data may further include a magnitude for each action, a magnitude of a force exerted as a result of an action, a setting of the control device associated with an action, a measure of a deviation from a constant pushing speed, and/or a measure of deviation from a constant pulling speed. The generated data may also include settings of the control device, where the settings store parameters associated with performing each action. There may be a finite number of settings of the control device associated with a single action. In other embodiments, there may be an infinite number of settings of the control device associated with a single action.

As shown in step 240, the method may include analyzing the data to determine a relation between the preceding status for each action and the plurality of actions. In some embodiments, the data may be analyzed to determine a relation between a preceding status for an action, the action, and the outcome of the action.

For example, the data may be used to determine a correlation between a particular preceding status and an action. This can be used to predict the occurrence of an action based on a particular preceding status. As another example, the data may be analyzed to determine a relation using data regressions, machine learning algorithms, and/or other data and/or statistical analysis tools.

In some embodiments, the captured medical image or sensor reading may be used in the determination of an outcome of an action, as discussed above. In some embodiments, the relation between the preceding status for each action, the plurality of actions, and/or the outcome may be based on the magnitudes of the plurality of actions, a magnitude of a force exerted as a result of an action, the settings of the plurality of actions, and/or the measures of deviation for the plurality of actions.

As shown in step 250, the method may include providing an evaluation of the user. For example, the evaluation of the user may be a comparison of the action to stored settings of what the action should be. An evaluation of the user may be a score or rating of the efficiency, precision, and/or accuracy of the action performed by a user. Furthermore, the evaluation of the user may be rating of the action performed by the user on a scale. Additionally, or alternatively, the evaluation of the user may be an evaluation of the user's performance of an action or of a procedure. A procedure may be evaluated as a combination of actions, where each action is a step in the procedure. In some embodiments, the evaluation of the user may be reported to the user via a user interface, such as the peripheral device 140 of FIG. 1, for example, visually and/or audibly.

In some embodiments, the steps of the method shown in FIG. 2 and discussed above, and variations thereof, may be performed for a second plurality of actions, for the same user, also referred to as first user, during a second procedure using the same endovascular device or a second endovascular device. The evaluation of the user may be configured to enable a device to analyze a prospective action of the same user. This evaluation may cause a correction to a prospective action of the user.

In some embodiments, the steps of the method shown in FIG. 2 and discussed above, and variations thereof, may be performed for a second plurality of actions, for a second user, during a second procedure using a second endovascular device.

The evaluation of the user may be configured to enable a device to analyze a prospective action of a second user. The evaluation of the first user may cause a correction to a prospective action of the second user. The correction may include impacting the endovascular device in response to the prospective action. For example, the prospective action of the second user may be an action utilizing a similar type of endovascular device and/or for the same type of medical indication.

For example, the prospective action of the second user may be an action configured to expand the distal mesh segment of an endovascular device. However, the evaluation of the first user may identify that the action following a shared preceding status between the first and second user should be a movement of the endovascular device forward into the body structure, and not an expansion of the distal mesh segment of the endovascular device. Thus, the evaluation of the user may cause the endovascular device to move forward into the body structure instead of expanding, effectively correcting, or overriding the action of the second user.

The evaluation of the first user may act as a template or gold standard to assist and/or guide a second user when performing the same or a similar invasive procedure as the first user. Accordingly, evaluation of the first and second users may act as a template or gold standard to assist and/or guide any subsequent user when performing the same or a similar invasive procedure as the first or second users. A correction to a prospective action may be a correction in response to a deviation from the prospective action from a pattern determined based on the data. The pattern may be determined by actions associated with a template or gold standard.

In some embodiments, the evaluation of a single user may include a comparison to the evaluations of actions of a group of users, wherein the group of users may comprise any number of users (e.g., 3, 4, 5, 10, 15, 20, 25, 50, 100 or more), where the single user is not included in the group of users. In other embodiments, the single user may be included in the group of users. For example, evaluations may be provided for a group of users. The evaluations may be set or considered as the template or gold standard for performing a type of invasive procedure. While the single user is performing the same type of invasive procedure, the actions of the single user may be compared to the evaluations of the group of users. The comparison may be used to provide an evaluation of the single user, where the evaluation is effectively a comparison to a template or gold standard.

In other embodiments, the steps of the method shown in FIG. 2 and discussed above, and variations thereof, may be performed for a group of individuals, such as for multiple users (e.g., 3, 4, 5, 10, 15, 20, 25, 50, 100 or more). In some embodiments, the evaluation of the first multiple users may be used as a part of a training protocol or as a gold standard when evaluating a second group of multiple users that are not part of the first multiple users. Furthermore, the aggregation of the evaluation of a first group of multiple users may allow for the evaluation of a second group of multiple users. The evaluation of the first multiple users may be used to provide a rating of the second group of multiple users. In other cases, the evaluation may be used as part of a training protocol to provide a safe and uniform practice for the second multiple users. Accordingly, the evaluation of the first multiple users and second group of multiple users may be used to provide an evaluation, rating, training protocol or as a gold standard for any subsequent group of multiple users.

Figure 3:
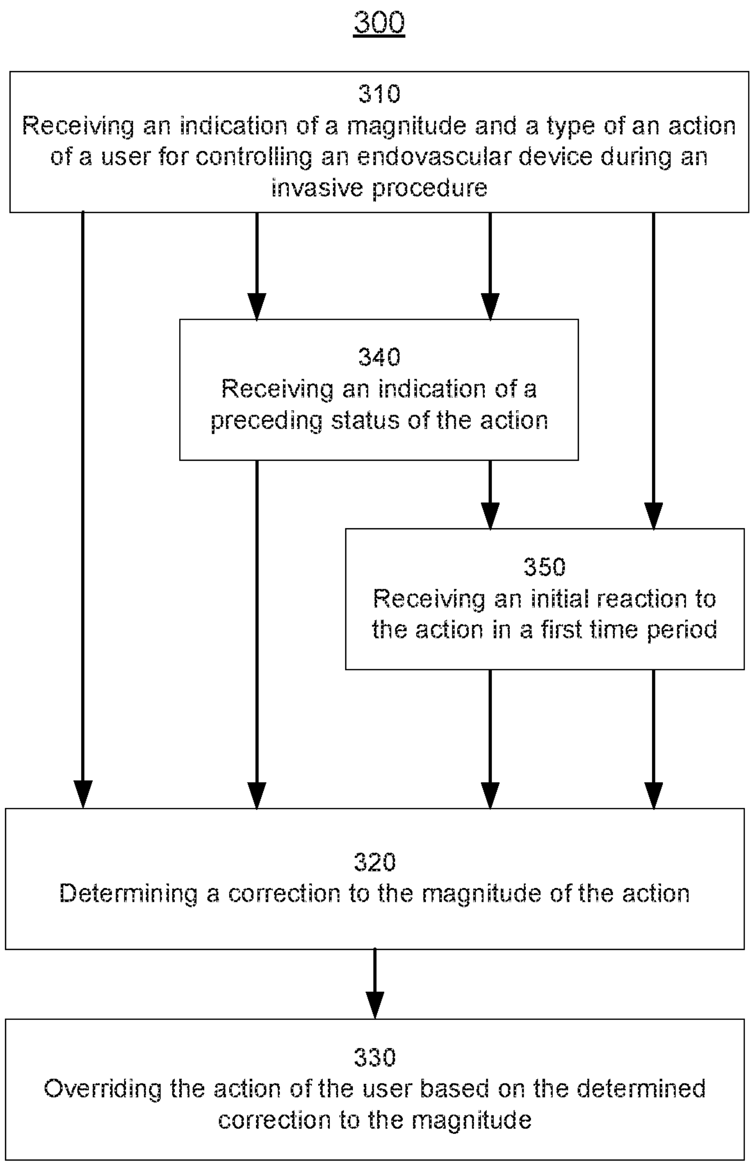
FIG. 3 presents a flowchart illustrating an example of a method for automatic correction of an action of a user of an endovascular device during an invasive procedure, consistent with various embodiments of the present disclosure.

FIG. 3 presents a flowchart illustrating an example of a method for automatic correction of an action of a user of an endovascular device during an invasive procedure 300, consistent with various embodiments of the present disclosure. The method shown in FIG. 3 and discussed below may be implemented as operations executed by a processor. The processor may be configured to execute instructions contained in a non-transitory computer readable medium. Alternatively, the processor may be part of a system.

As shown in step 310, the method may include receiving an indication of a magnitude and a type of an action of a user for controlling an endovascular device during an invasive procedure. According to some embodiments, the action may be a continuous action. According to other embodiments, the action may be a non-continuous action. The magnitude of an action may include a direction, a curvature, a net force, a speed, or other characterizations of a transformation of an endovascular device. The type of an action may be a characterization of an action. For example, a type of action may be an expansion of the distal portion of an endovascular device (e.g., a mesh segment). The magnitude may then be the degree of expansion or the force exerted on a body structure (e.g., on a blood vessel).

As shown in step 320, the method may include determining a correction to the magnitude of the action. For example, the action may be a movement of an endovascular device in a first direction. A determined correction may include identifying that the movement of the endovascular device should be in a second direction, as opposed to the first direction.

In some embodiments, an action may be an expansion of a mesh of an endovascular device (e.g., of a stent retriever or of an adjustable mesh device). A determined correction may include identifying that the mesh segment of the device is expanded to a size which may be too small to capture a clot in a body structure (e.g., blood vessel) or to dilate a narrowing in a body structure (e.g., blood vessel).

In some embodiments, an action may be a contraction of a mesh of an endovascular device (e.g., of a stent retriever or of an adjustable mesh device). A determined correction may include identifying that the mesh segment of the device is expanded to a size that may be harmful to the body structure (e.g., blood vessel).

The determined correction may be based on the type of the action and one or more parameters associated with the type of action. Each parameter of the one or more parameters may be associated with a different magnitude of an action. The parameters may be stored correlations between a type of action and a desired magnitude of the action, where the parameters are stored in a memory device. The memory device may be part of a control device 110 or of peripheral device 140 of FIG. 1.

In some embodiments, the determination of the correction may further be based on a standard of care. For example, in embolization of an aneurysm, the standard of care may include a packing density (e.g., of coils) of greater than or equal to 19%. The packing density included in the standard of care may vary based on factors such as, but not limited to, the size, type, and location of the aneurysm. The determination of the correction may be based, for example, on a comparison of a packing density during a coil embolization procedure to the packing density required by the standard of care.

As shown in step 330, the method may include overriding the action of the user based on the determined correction to the magnitude. For example, an override may be configured to modify a particular magnitude when the action is configured to exert a net force of the particular magnitude on a core wire (e.g., a control wire) of the endovascular device. According to some embodiments, and without limitation, the core wire may be a wire capable of causing an expansion and/or a contraction of a mesh segment of a controllable endovascular device. According to other embodiments, and without limitation, the core wire may be a wire capable of causing a controllable bend in at least one distal portion (e.g., distal tip) of an endovascular device.

Other examples of overriding may include modifying one or more of: a force in a direction of movement, a magnitude of electric current flow, a rate of heating, a temperature, a curvature of a distal portion (e.g., distal tip), a formation (e.g., expansion or contraction) of a distal portion of the endovascular device (e.g., mesh segment), a speed of movement, a distance of movement, a direction of movement, a rate of detachment, and/or a location of detachment. Another example of overriding may include smoothing a time series of magnitudes where the action is associated with a time series of magnitudes (e.g., pulsatile motion, such as but not limited to, repeated expansion and contraction of a mesh segment for integration of a clot).

In some embodiments, an action may be associated with a first parameter of the control device. The override may be configured to avoid the action associated with the first parameter of the control device and to cause a second action associated with a second parameter of the control device.

For example, and continuing the coil embolization example discussed above, the action may be a detachment of the coil in an embolization. However, the determined correction may indicate that the packing density of the coil in the aneurysm has not reached a packing density defined by the standard of care. Accordingly, the override may include preventing the action, where the action is the detachment of the coil in the aneurysm, and instead cause the coil to continue filling the aneurysm.

In some embodiments, the correction to the magnitude of the action to the user may be reported to the user. The correction may be reported to the user, for example, via a user interface or a display, such as the peripheral device 140 of FIG. 1, (e.g., by visual and/or audible means).

As shown in step 340, the method may further include receiving an indication of a preceding status of the action. The correction determined in step 320 may then be based on the type of action, the preceding status, and/or on one or more parameters associated with the type of action. The overriding of step 330 may be based on the determined correction that includes the preceding status in the determination.

As shown in step 350, the method may further include receiving an initial reaction to the action in a first time period. An initial reaction to the action may be a resistance due to the endovascular device interacting with a narrowed body structure, such as but not limited to, a narrowed blood vessel, or resistance due to the endovascular device interacting with a clot (such as a blood clot). In another example, an initial reaction to the action may be a speed that the endovascular device travels through a body structure, such as but not limited to, a blood vessel. According to one embodiment, the method may further include receiving a reaction to the action in a second, third, fourth, fifth or more time periods.

After receiving the initial reaction, the correction determined in step 320 may then be based on the type of action, the initial reaction to the action, and/or on one or more parameters associated with the type of action. In other embodiments, the correction determined in step 320 may be based on the type of action, the preceding status, the initial reaction to the action, and/or on one or more parameters associated with the type of action. The overriding of step 330 may be based on the determined correction that includes the preceding status and the initial reaction in the determination. In other embodiments, the overriding of step 330 may be based on the determined correction that includes the initial reaction and not the preceding status in the determination. The overriding of the action 330 may occur after the first time period. Furthermore, the overriding of the action 330 may occur after a second, third, fourth, fifth or more time periods.

Figure 4:
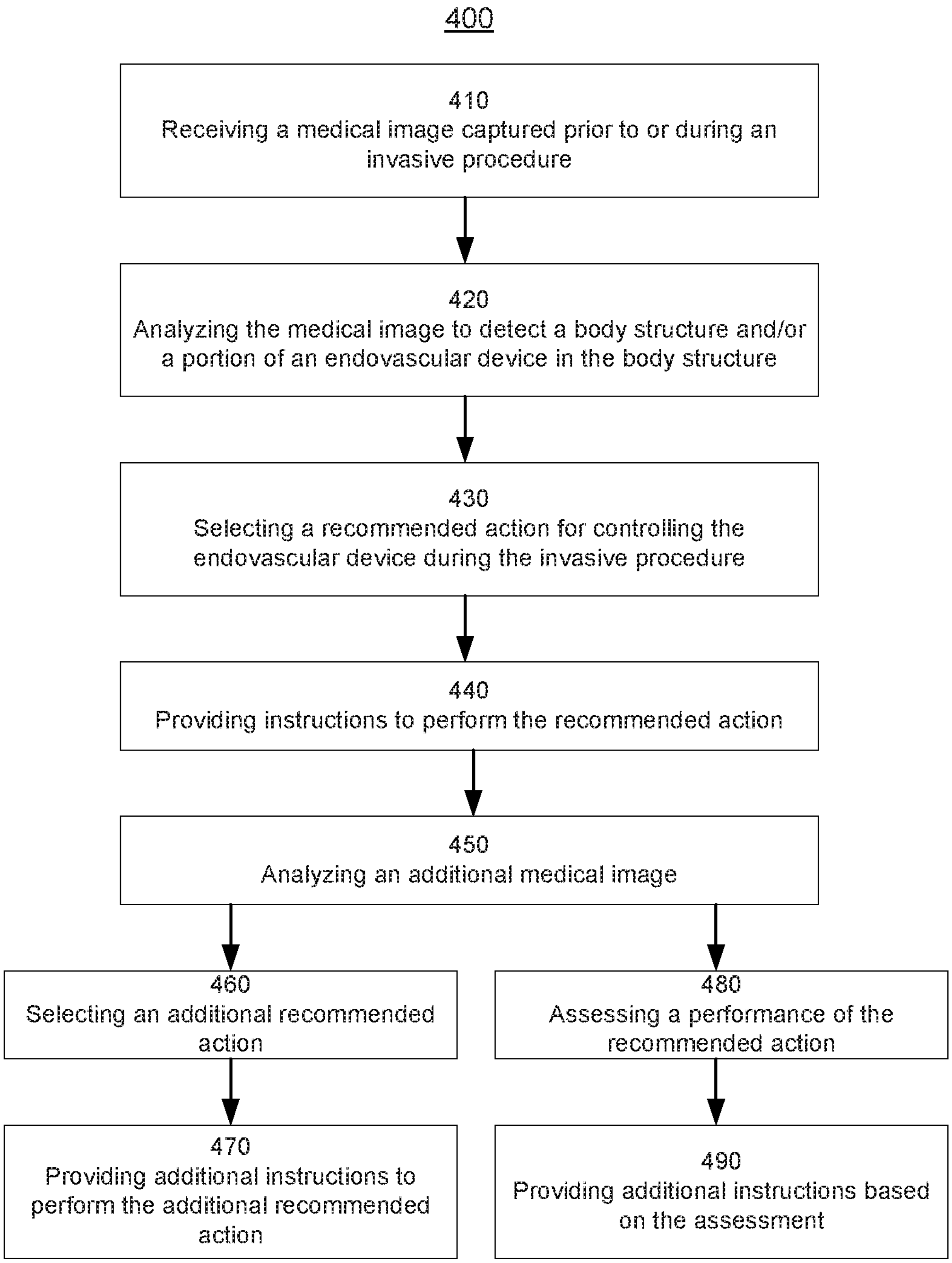
FIG. 4 presents a flowchart illustrating an example of a method for recommending an action during an endovascular procedure, consistent with various embodiments of the present disclosure.

FIG. 4 presents a flowchart illustrating an example of a method for recommending an action during an endovascular procedure 400, consistent with various embodiments of the present disclosure. The method shown in FIG. 4 and discussed below may be implemented as operations executed by a processor. The processor may be configured to execute instructions contained in a non-transitory computer readable medium. Alternatively, the processor may be part of a system.

As shown in step 410, the method may include receiving a medical image captured prior to or during an invasive procedure. The at least one medical image may be captured prior to the procedure showing a condition of a site in the patient's body to be treated during the procedure. Prior to an invasive procedure may refer to a time period before the invasive procedure is performed, before an endovascular device is inserted into the patient, and/or before the endovascular device reaches a certain location in the body of the patient. The method may include analyzing the medical image to detect a body structure and/or a portion of an endovascular device in the body structure, as shown in step 420.

The analyzing of the medical image may include calculating a convolution of at least part of the medical image. The calculated convolution may be used to detect a body structure and/or a portion of an endovascular device in the body structure. The medical image may be analyzed to determine a magnitude or direction of a force necessary for an action. In other embodiments, the medical image may be analyzed to detect an aneurysm in the body structure. In some embodiments, the medical image may be analyzed to detect a narrowing in a blood vessel or occlusion in a blood vessel. In other embodiments, the medical image may be analyzed to detect tortuous anatomy.

As shown in step 430, the method may include selecting a recommended action for controlling the endovascular device during an invasive procedure. The recommended action may be selected based on the detected body structure and/or the portion of the endovascular device in the body structure. The selection of the recommended action may be based on stored parameters associating a state of the detected body structure and/or the detected portion of the endovascular device and a desired action.

Recommended actions may include actions that transform the endovascular device. Examples of transformations include, but are not limited to, exerting a magnitude of a force on the endovascular device, changing a magnitude of a force exerted on the endovascular device, causing a flow of electric current between two electrodes positioned within a body structure, causing a difference of electrical potential between two electrodes positions within a body structure, heating up a portion of the endovascular device, bending a distal portion of the endovascular device, expanding or contracting a distal portion of an endovascular device, and other movements or physical alterations of the endovascular device. In some embodiments, the recommended action may include a repetitive action, such as a pulsatile motion (e.g., repeated expansion and contraction, where the repeated expansion and contraction may be for a predetermined time period) of a distal portion of an endovascular device (e.g., of a mesh segment of an endovascular device).

In some embodiments, the medical image may be analyzed to identify a curvature of a body structure. The recommended action may include bending of at least one distal portion of an endovascular device (e.g., by exerting a force on a core wire of the endovascular device), where the curvature of the bending is determined by the curvature of the body structure.

In other embodiments, the medical image may be analyzed to identify a branching of the body structure to at least two branches. One of the branches may be selected and a curvature may be determined based on the branch. The recommended action may include bending of at least one distal portion of an endovascular device (e.g., by exerting a force on a core wire of the endovascular device), where the curvature of the bending is determined by the determined curvature.

In some embodiments, the medical image may be analyzed to detect a clot in the body structure and the recommended action, such as a degree of expansion of a distal portion of the endovascular device or a pulsatile motion of the endovascular device, may be selected further based on the clot (e.g., such as on the type of clot, its location, and its size).

In other embodiments, the medical image may be analyzed to detect a degree of packing in an aneurysm and the recommended action, such as a detaching of the coil, may be selected further based on the degree of packing. Furthermore, the medical image may be analyzed to detect an aneurysm in a body structure.

Furthermore, the medical image may be analyzed to detect a narrowing in the body structure, such as during vasospasm or atherosclerosis. The selection of the recommended action may be further based on the narrowing of the body structure, such as for example, on the type and location of the narrowing.

In other embodiments, the medical image may be analyzed to determine a likelihood of an impending change in a spatial arrangement of parts of the endovascular device to an undesired spatial arrangement. A recommended action may be selected based on the reduction of a likelihood of the impending change.

In some embodiments, a recommended action may include expanding or contracting a distal portion of an endovascular device (e.g., a mesh segment by e.g., exerting a force on a core wire of the endovascular device). The expansion or contraction may be to a particular formation, and the particular formation may be determined based on the analysis of the medical image. For example, the analysis of the medical image may determine a diameter of a narrowed body structure (e.g., a blood vessel). Accordingly, the recommended action may be a contraction of an endovascular device to a desired diameter based on the diameter of the narrowed body structure (e.g., a blood vessel). This may allow the endovascular device to advance through tortuous anatomy in the body of a patient. According to some embodiments, the recommended action may be a contraction of an endovascular device to a desired diameter to allow the endovascular device to retract safely from the body structure (e.g., blood vessel) of a patient.

Furthermore, the medical image may be analyzed to determine a recommended action involving moving the endovascular device according to one or more of the following: a speed of movement of the endovascular device, a distance of movement of the endovascular device, a direction of movement of the endovascular device, and/or a prevention of a particular movement of the endovascular device.

In some embodiments, a second endovascular device may be introduced and/or present in the body structure. The medical image may be analyzed to detect the second endovascular device in the body structure. The selection of the recommended action for controlling the first endovascular device may be further based on the state and/or location of the second endovascular device, and vice versa.

In other embodiments, the medical image may be analyzed to detect a portion of the second endovascular device in the body structure. The selection of the recommended action for controlling the first endovascular device may be further based on the detected portion of the second endovascular device. The detected portion of the endovascular device (or the second endovascular device) may include one or more of the following: a proximal marker, a distal marker, a catheter marker, a sheath marker, an aspiration catheter marker, a marker on a bendable portion of the second endovascular device, and/or a marker on an expandable portion of the second endovascular device.

In other embodiments, the medical image may be analyzed to detect a portion of one or more additional endovascular devices used in the medical procedure. The selection of the recommended action for controlling any of one or more of a first, second, third, and so forth endovascular device may be further based on the detected portion of any of the endovascular devices used in the medical procedure.

As shown in step 440, the method may include providing a set of instructions to perform the recommended action. The instructions may include an instruction configured to cause the control device to transform the endovascular device. Furthermore, the instruction may include an indication of a desired parameter of the control device. A desired parameter may include, for example, a desired curvature of the guide wire or guide catheter, a desired expanded or contracted state of the mesh segment of the stent retriever or of the adjustable mesh device, a desired location of the endovascular device, a desired amount of coil for an embolism, a desired temperature of the endovascular device during endovascular warming to treat hypothermia.

In some embodiments, the set of instructions may be provided to the user. For example, the set of instructions may be provided to the user via a user interface, such as the peripheral device 140 of FIG. 1. Furthermore, the set of instructions may be presented to the user visually and/or audibly. The medical image, in addition to the set of instructions, may be provided to the user. In other embodiments, the medical image, and not the set of instructions, may be provided to the user. In other embodiments, the instructions may be presented on the medical image (e.g., a marking of a desired location for placement of the endovascular device, a marking of the size of expansion/collapse of the mesh segment of the endovascular device, a marking of a desired curvature of a medical device).

As shown in step 450, the method may include receiving and analyzing an additional medical image. The additional medical image may be captured after the set of instructions were provided. This may provide an evaluation of a particular action after the performance of said action.

As shown in step 460, in some embodiments, the method may include selecting an additional recommended action. The additional recommended action may be selected based on the analysis of the additional medical image. As shown in step 470, the method may include providing additional instructions to perform the additional recommended action. The additional instructions may be generated and provided by performing steps 410-440 using the additional medical image.

As shown in step 480, in other embodiments, the method may include assessing a performance of the recommended action. The assessment may be based on the analysis of the additional medical image. As shown in step 490, an additional set of instructions configured to perform the additional recommended action may be provided. The additional set of instructions may be generated and provided by performing steps 410-440 using the additional medical image, where the performance of the recommended action may be included in the analyzing 420 and selecting 430.

Further, in some embodiments, the assessing of the performance of an action 480 and the selecting of an additional action 460 may both be performed and additional instructions 470 and/or 490 may be provided based on the assessment 480 and selection 460.

Figure 5:
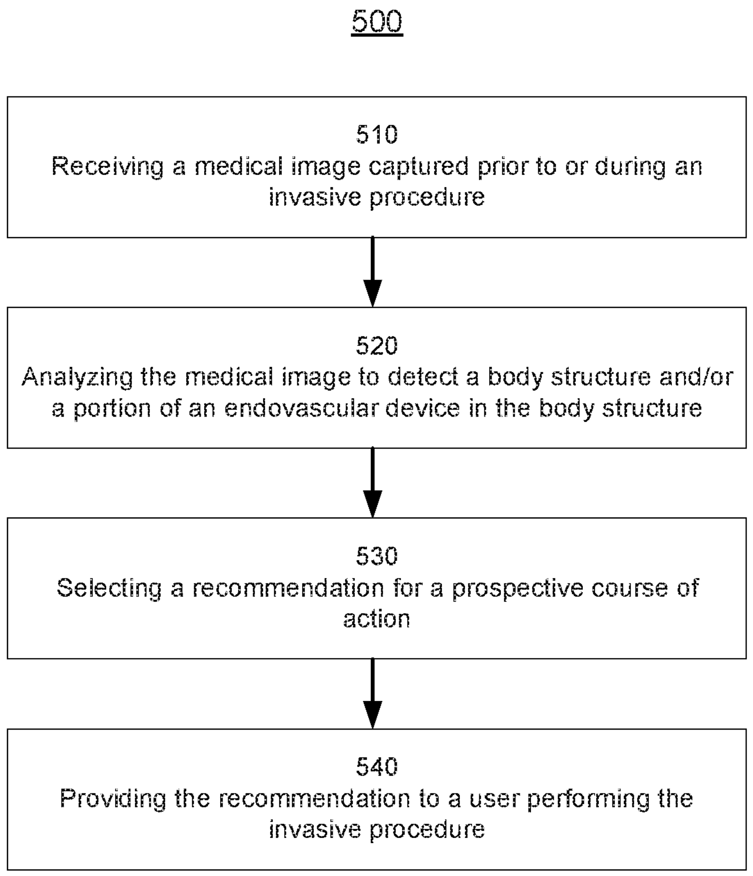
FIG. 5 present a flowchart illustrating an example of a method for providing at least one recommendation to a user during an endovascular procedure, consistent with various embodiments of the present disclosure.

FIG. 5 presents a flowchart illustrating an example of a method for providing at least one recommendation to a user during endovascular procedures 500, consistent with various embodiments of the present disclosure. The method shown in FIG. 5 and discussed below may be implemented as operations executed by a processor. The processor may be configured to execute instructions contained in a non-transitory computer readable medium. Alternatively, the processor may be part of a system.

As shown in step 510, the method may include receiving a medical image captured prior to or during an invasive procedure. The method may include analyzing the medical image to detect a body structure and/or a portion of an endovascular device in the body structure, as shown in step 520.

As shown in step 530, the method may include selecting a recommendation for a prospective course of action. The selection of the recommendation for a prospective course of action may be based on the detected body structure and/or a portion of the endovascular device in the body structure.

The recommendation for a prospective course of action may include a recommendation of a specific device to use, such as a catheter (e.g., aspiration catheter or guide catheter), a microcatheter, a stent retriever (e.g., a controllable stent retriever), a stent, an adjustable mesh device, a guide wire (e.g., a controllable guide wire), and/or other intraluminal or endovascular device, or of a specific size of the endovascular device to use. Additionally, or alternatively, the recommendation may include a location the endovascular device should be placed in the body structure (e.g., in reference to a clot or narrowing in a body structure, or in reference to an aneurysm). The recommendation may also include a rotational angle and location in which bending should be implemented to advance through tortuous anatomy. Furthermore, the recommendation may include a size to open the mesh to integrate a clot and a size to close, or contract, the mesh to remove the clot. Additionally, or alternatively, the recommendation may be a particular retrieval speed and/or retrieval force.

Furthermore, as shown in step 540, the method may include providing the recommendation to a user performing the invasive procedure.

Figure 6:
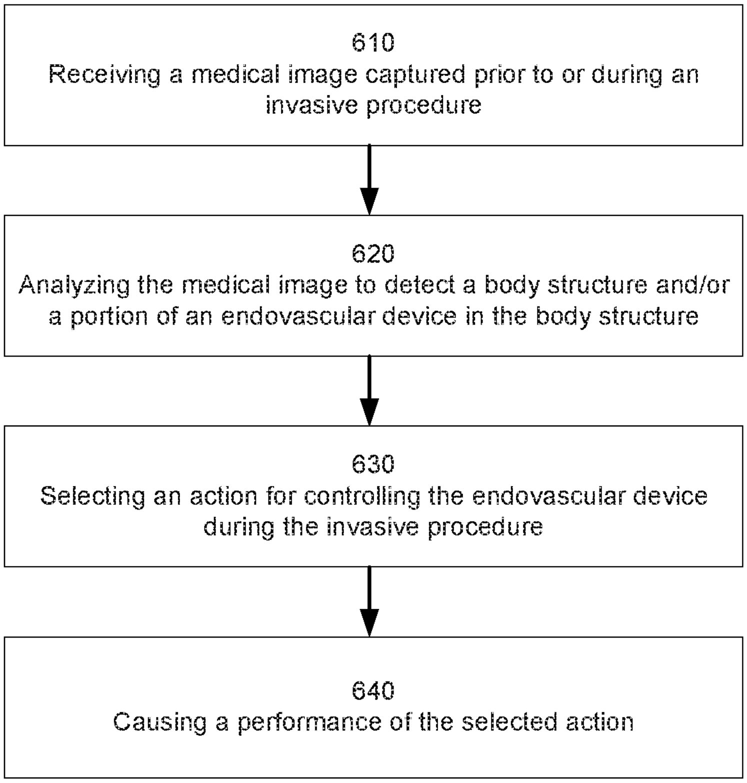
FIG. 6 presents a flowchart illustrating an example of a method for automation of an endovascular procedure, consistent with various embodiments of the present disclosure.

FIG. 6 presents a flowchart illustrating an example of a method for automation of an endovascular procedure 600, consistent with various embodiments of the present disclosure. The method shown in FIG. 6 and discussed below may be implemented as operations executed by a processor. The processor may be configured to execute instructions contained in a non-transitory computer readable medium. Alternatively, the processor may be part of a system.

As shown in step 610, the method may include receiving a medical image captured prior to or during an invasive procedure. The method may include analyzing the medical image to detect a body structure and/or a portion of an endovascular device in the body structure, as shown in step 620. A body structure size, body structure diameter, a type of body structure narrowing, an extent of body structure narrowing, a clot size, and/or a clot type may be determined based on the detected body structure and/or portion of the endovascular device.

As shown in step 630, the method may include selecting an action for controlling the endovascular device during the invasive procedure. The selection may be based on the detected body structure and/or the portion of the endovascular device in the body structure. In some embodiments, the selected action may be an expansion or contraction of a distal portion of the endovascular device. In other embodiments, the selected action may be a change in a speed of pushing or speed of pulling of the endovascular device. The selected action may include a change in frequency of the expansion or contraction of a distal portion of the endovascular device. The selected action may also include an activation of an aspiration catheter. Furthermore, the selected action may include a bending of at least one distal portion of the endovascular device. As shown in step 640, the method may include causing the performance of the selected action.

Performance of the selected action may include instructions configured to control the endovascular device, where the instructions include one or more parameters associated with the selected action. For example, the selected action may include a bending of a distal portion of the endovascular device. The instructions may include parameters indicating the desired bending curvature and speed of bending. The endovascular device may perform the selected action in accordance with the one or more parameters included in the instructions.

Additional embodiments of method of automation of an endovascular procedure may include or involve any of the above-mentioned steps illustrates in FIGS. 1-6 and any of the discussed variations thereof.

In some embodiments, an automation may include a user providing information for performing an action or procedure and the action or procedure proceeding automatically (i.e., without user intervention). Examples of procedures may include, but are not limited to, clot retrieval, dilation of narrowed body structures (e.g., blood vessels), vessel remodeling for support of embolism for treatment of aneurysm, and endovascular coiling for treating aneurysms. In some embodiments, an automation may include parts of the medical procedure discussed above, such as but not limited to, moving the endovascular device forward (e.g., to a desired site within the body of a patient); retracting the endovascular device out of the body structure (e.g., at a constant force and/or speed); expanding or collapsing a mesh segment of the endovascular device to a desired diameter; exerting a pulsatile motion, such as but not limited to, expansion and contraction of a mesh segment for integration of a clot; activating suction in an aspiration catheter; and/or causing a bend in at least one distal portion of a guide wire or a guide catheter.

According to some embodiments, a user may mark a treatment site on or based on a medical image and the endovascular device may navigate to the treatment site, where the endovascular device is controlled by a control device, such as control device 110. The user may designate a type of procedure required and the endovascular device, controlled by a control device such as control device 110, may automatically navigate to a site of treatment. Furthermore, in some embodiments, the procedure may be performed automatically by the endovascular device, controlled by a control device such as control device 110, after a designated treatment site and/or type of procedure is indicated or required.

In some embodiments, a user may designate specific parameters such as the size of a clot, diameter of a body structure (e.g., a blood vessel), extent of a mesh expansion required, length of time required to integrate a clot by pulsatile motion, size of an aneurysm, and/or other indicators of the state of the body structure and/or endovascular device. The endovascular device, controlled by the control device, may then carry out a procedure, where the procedure uses the designated specific parameters in guiding the procedure.

Furthermore, in other embodiments, the user may perform a procedure in the body of a patient. The automation may then perform the retrieval of the device from the body of the patient at a constant speed and force.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, any of the methods and steps discussed above, and variations thereof, may be combined in any fashion. While certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps. Furthermore, the subject matter disclosed and claimed as features of a system or non-transitory computer readable medium may also be practiced as steps of a method, and vice versa.

The features and advantages of the disclosure are apparent from the detailed specification, and thus, it is intended that the appended claims cover all systems and methods falling within the true spirit and scope of the disclosure. As used herein, the indefinite articles “a” and “an” mean “one or more.” Similarly, the use of a plural term does not necessarily denote a plurality unless it is unambiguous in the given context. Words such as “and” or “or” mean “and/or” unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Throughout this application, various embodiments of the present disclosure may be presented in a range format. It should be understood that the description in range format is merely for convenience and brevity and should not be construed as an inflexible limitation on the scope of the present disclosure. Accordingly, the description of a range should be considered to have specifically disclosed all the possible subranges as well as individual numeric values within that range. For example, description of a range such as from 1 to 6 should be considered to include subranges such as from 1 to 3, from 1 to 4, from 1 to 5, from 2 to 4, from 2 to 6, from 3 to 6, and so forth, as well as individual numbers within that range, for example, 1, 2, 3, 4, 5, and 6. This applies regardless of the breadth of the range.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A non-transitory computer readable medium containing operations that when executed by at least one processor, cause the at least one processor to analyze actions of a user of an endovascular device during an invasive procedure, the operations comprising:
- receiving indications of a plurality of actions of the user for controlling the endovascular device during the invasive procedure using a control device of the endovascular device;
- receiving an indication of a preceding status for each action of the plurality of actions;
- generating data related to the plurality of actions of the user, the data including a type of action and the preceding status for each action;
- analyzing the data to determine a relation between the preceding status for each action and the plurality of actions;
- using the determined relation between the preceding status for each action and the plurality of actions to provide an evaluation of the user, wherein the evaluation specifies a standard for the user to meet;
- based on the evaluation of the user, determining a control action for controlling the endovascular device during the invasive procedure, wherein the control action enables the user to meet the standard;
- transmitting an instruction to the endovascular device via the control device, wherein the instruction causes the endovascular device to perform the control action;
- receiving a sensor reading from a sensor, the sensor reading being captured after the control action, wherein the sensor is mechanically connected to the endovascular device to allow the sensor to sense a state of the endovascular device; and
- analyzing the sensor reading to determine an outcome of the control action, wherein the outcome correlates the state of the endovascular device to the control action.

2. The non-transitory computer readable medium of claim 1, the operations further comprising:
- generating the data related to the plurality of actions of the user, the data including an outcome for each of the plurality of actions;
- analyzing the data to determine a relation among the preceding status for each action, the plurality of actions, and the outcome; and
- using the determined relation among the preceding status for each action, the plurality of actions, and the outcome to provide the evaluation of the user.

3. The non-transitory computer readable medium of claim 2, the operations further comprising:
- receiving a medical image captured after a particular action of the plurality of actions; and
- analyzing the medical image to determine an outcome of the particular action.

4. The non-transitory computer readable medium of claim 1, wherein the outcome comprises a modification to one or more of a physical state of a patient and a modification to the state of the endovascular device.

5. The non-transitory computer readable medium of claim 1, wherein the outcome occurs 1 second to 2 minutes after the control action.

6. The non-transitory computer readable medium of claim 1, wherein the outcome has an effect on a prognosis.

7. The non-transitory computer readable medium of claim 1, wherein the data further comprises a magnitude for each action of the plurality of actions, and wherein the relation is further based on magnitudes of the plurality of actions.

8. The non-transitory computer readable medium of claim 1, wherein the data further comprises for each action of the plurality of actions a setting of the control device associated with the action, and wherein the relation is based on settings of the plurality of actions.

9. The non-transitory computer readable medium of claim 1, wherein the data further comprises for each action of the plurality of actions a measure of deviation from a constant pulling speed, the relation being based on measures of deviation for the plurality of actions.

10. The non-transitory computer readable medium of claim 1, wherein the provided evaluation of the user is configured to enable a device to analyze a prospective action of the user.

11. The non-transitory computer readable medium of claim 10, wherein the provided evaluation of the user is configured to cause a correction to the prospective action of the user.

12. The non-transitory computer readable medium of claim 1, the operations further comprising:
- receiving a medical image captured before a particular action of the plurality of actions; and
- analyzing the medical image to determine a preceding status of the particular action.

13. The non-transitory computer readable medium of claim 1, wherein the sensor reading is a first sensor reading, the operations further comprising:
- receiving a second sensor reading captured from the sensor before a particular action of the plurality of actions, wherein the second sensor reading is from a sensor that is connected to the endovascular device; and analyzing the second sensor reading to determine a preceding status of the particular action.

14. The non-transitory computer readable medium of claim 1, wherein the preceding status for each action comprises a degree of opening associated with the endovascular device.

15. The non-transitory computer readable medium of claim 1, wherein the preceding status for each action comprises a position of the endovascular device.

16. The non-transitory computer readable medium of claim 1, wherein the preceding status for each action comprises at least one of a type of a clot, a location of the clot, or a size of the clot.

17. The non-transitory computer readable medium of claim 1, wherein the preceding status for each action comprises one or more of a size of a body structure at a site of treatment and a location of the site of treatment.

18. The non-transitory computer readable medium of claim 1, wherein the plurality of actions includes an action configured to cause a distal portion of the endovascular device to bend.

19. The non-transitory computer readable medium of claim 1, wherein the plurality of actions includes an action configured to cause a distal portion of the endovascular device to expand or contract.

20. The non-transitory computer readable medium of claim 1, wherein the plurality of actions includes an action configured to cause a detachment of an intraluminal device in a body structure of a patient.

21. The non-transitory computer readable medium of claim 1, wherein the plurality of actions includes an action configured to cause a movement of the endovascular device.

22. The non-transitory computer readable medium of claim 1, wherein the plurality of actions includes an action configured to cause at least one of an electric current to flow between two electrodes positioned within a body structure or a difference of electrical potential between the two electrodes positioned within the body structure.

23. The non-transitory computer readable medium of claim 1, wherein the plurality of actions includes an action configured to cause a portion of the endovascular device to heat up.

24. The non-transitory computer readable medium of claim 1, wherein the plurality of actions includes an action configured to cause a detachment of a stent in a body structure of a patient.

* * * * *